United States Patent [19]

Gaba

[11] Patent Number: 5,395,338
[45] Date of Patent: Mar. 7, 1995

[54] SURGICAL INSTRUMENT SHARP END FOIL

[76] Inventor: Rodolfo Gaba, 722 Harper St., Simi Valley, Calif. 93065

[21] Appl. No.: 275,258

[22] Filed: Jul. 15, 1994

Related U.S. Application Data

[63] Continuation of Ser. No. 94,842, Jul. 20, 1993.

[51] Int. Cl.$^6$ .............................................. A61M 5/00
[52] U.S. Cl. .................................... 604/110; 206/366
[58] Field of Search ............... 604/110, 187, 192, 263; 206/364, 365, 366

[56] References Cited

U.S. PATENT DOCUMENTS

| | | | |
|---|---|---|---|
| 4,798,587 | 1/1989 | Willooghby | 604/110 |
| 4,986,811 | 1/1991 | Thread et al. | 604/110 |
| 4,995,871 | 2/1991 | Sasaki et al. | 604/110 |
| 5,187,850 | 2/1993 | McCammon et al. | 604/110 X |

*Primary Examiner*—John D. Yasko
*Attorney, Agent, or Firm*—Poms, Smith, Lande & Rose

[57] ABSTRACT

A surgical instrument sharp end foil for receiving and trapping the free end of a surgical instruments sharp such as a syringe needle, said sharp having a restrained end opposite said free end and a longitudinal axis extending between said restrained and free ends, said foil comprising a housing having a sharps receiving portion, a gripping element for engaging the free end of the chosen sharp, a wedging element for engaging the gripping element, and a biasing element for urging the wedging element and the gripping element into engagement.

The wedging element is configured to communicate with the gripping element such that, upon insertion of the free end of the sharp into the housing, the gripping element exerts a force against the free end having a component which is perpendicular to the longitudinal axis of the sharp and such that a longitudinal movement of the sharp tending to withdraw the free end of the sharp from the housing causes the component of force perpendicular to the longitudinal axis of the sharp to increase so as to frictionally interfere with the withdrawal thereof.

The gripping element is also provided with mechanical interference means such that a longitudinal movement tending to withdraw the free end of the sharp from the housing causes the gripping element to distort the free end of the sharp so as to mechanically interfere with the withdrawal thereof.

The foil may also be provided with a sealing element to seal the tips of sharps having tubular end sections wherein residual bodily fluids may reside.

6 Claims, 2 Drawing Sheets

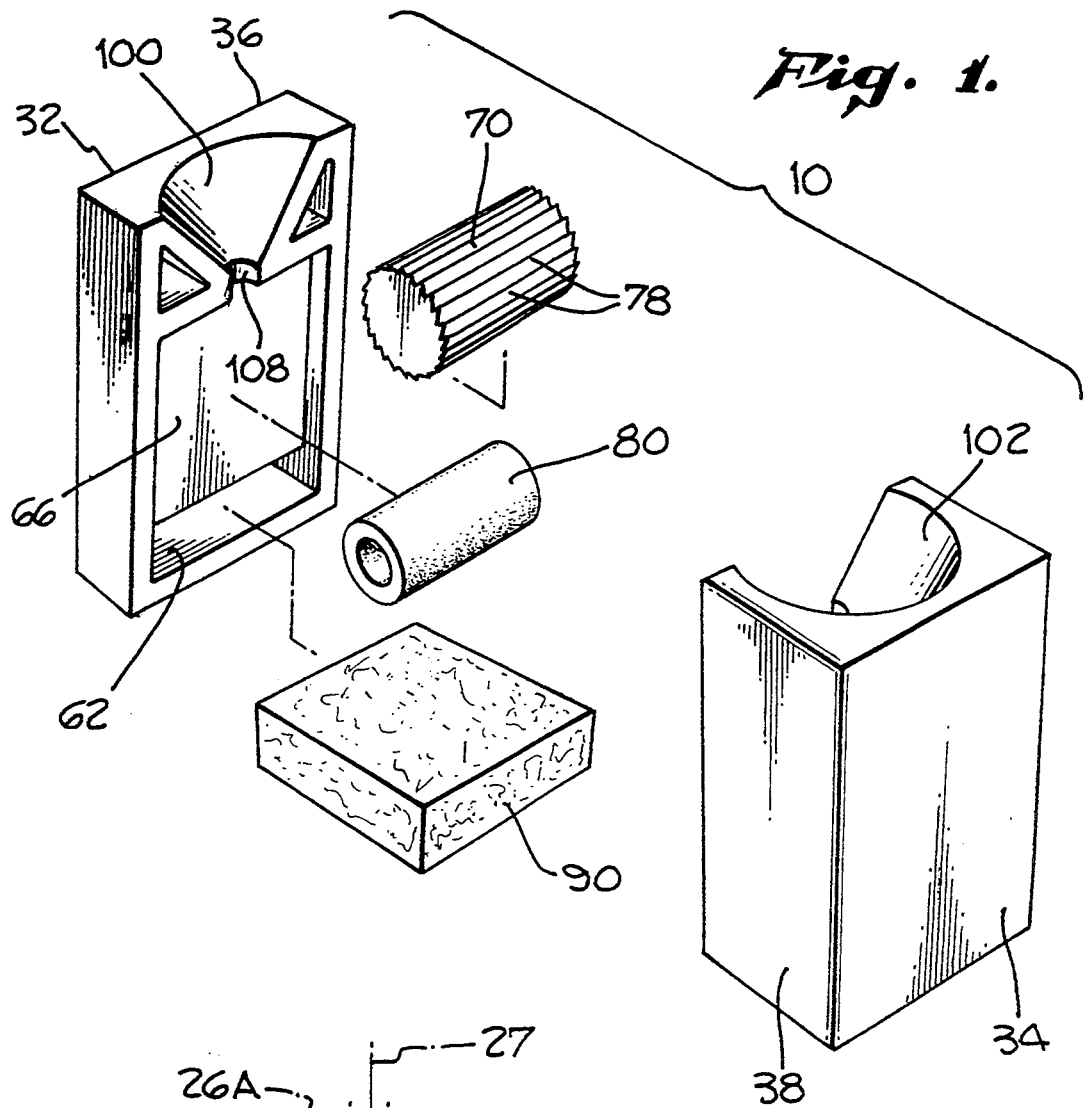
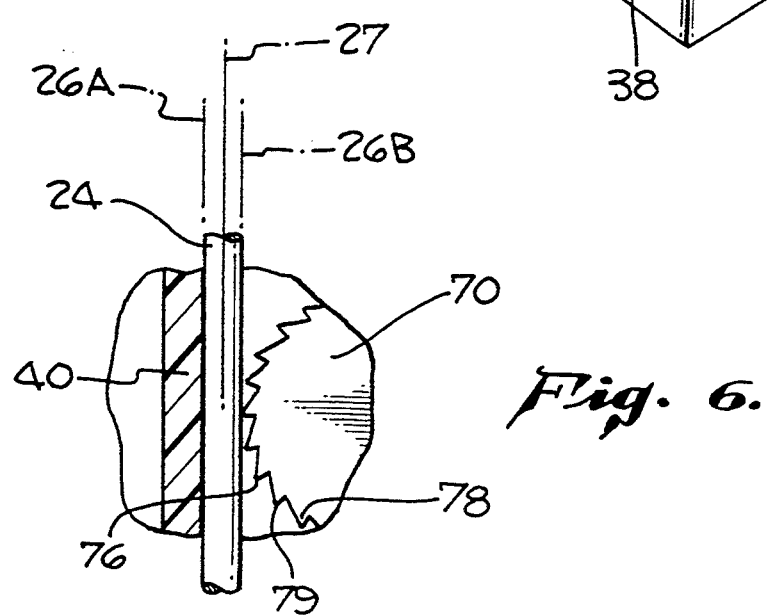

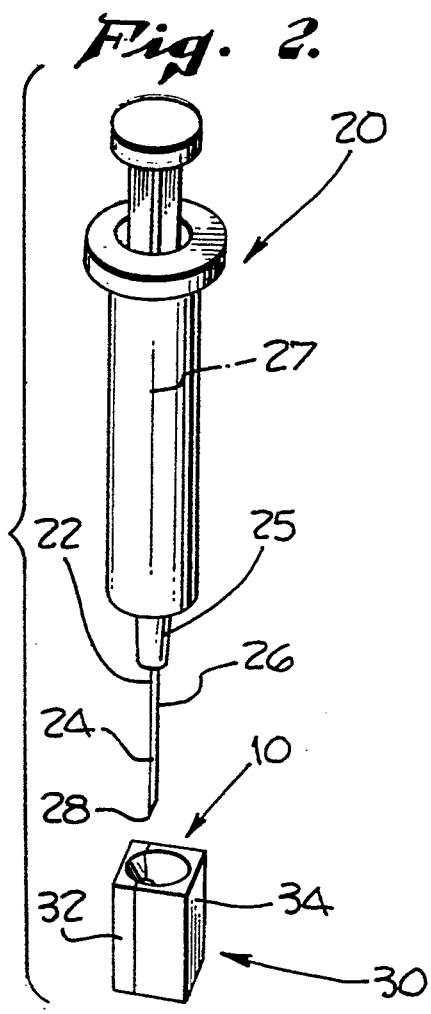
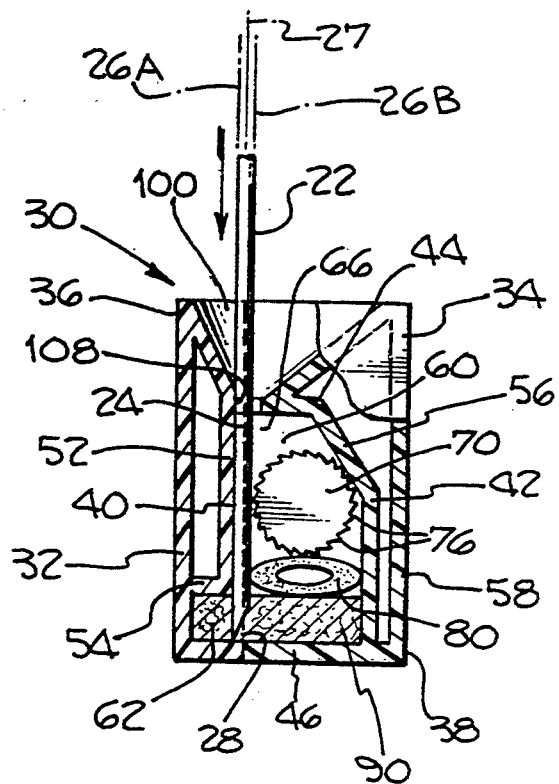
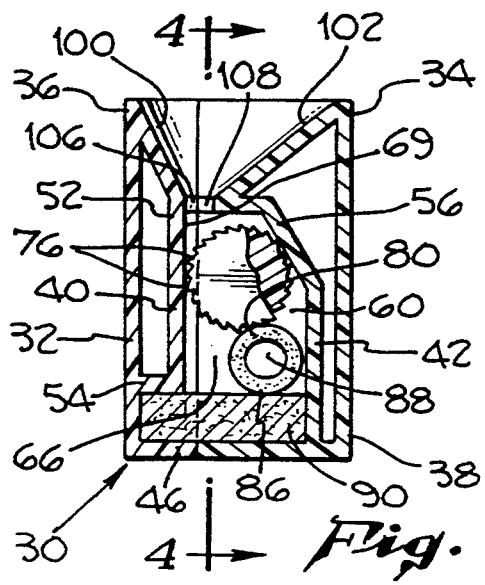
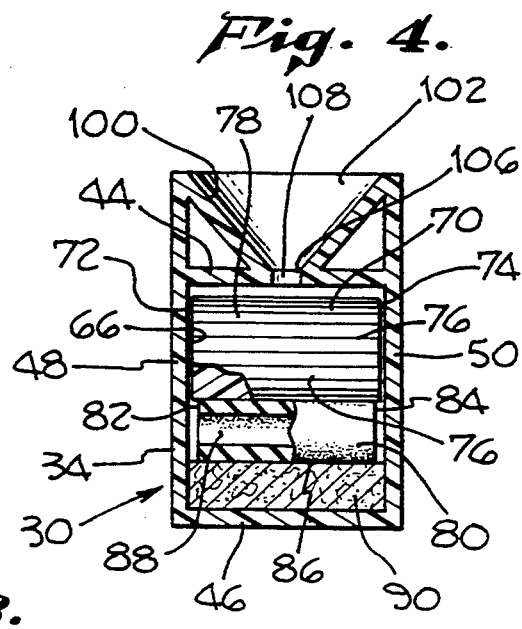

SURGICAL INSTRUMENT SHARP END FOIL

RELATED PATENT APPLICATIONS

This is a continuation application of Ser. No. 08/094,842, filed Jul. 20, 1993.

BACKGROUND OF THE INVENTION

1. Field of Invention

The present invention relates generally to medical-surgical product disposal devices used in hospitals, infirmaries, and doctors' offices, and more particularly to a device for permanently capping the contaminated end of disposable surgical sharps such as hypodermic needles.

2. Description of Related Art

During the past ten years, the medical care providers have employed disposable, one-time-use only, medical-surgical devices and materials with increasing frequency. This trend is away from the former procedure of sterilization and re-use of these devices, both for reasons of expense and sterility.

Present protocol in those institutions employing the use-and-dispose philosophy entails the use of a single container to hold and dispose of a multitude of small sharp implements, e.g., hypodermic needles, trocars, stylers, etc., employed in surgical procedures, along with other medical waste such as dressings, cotton applicators and the like.

This method of depositing a multitude of medical waste products renders it virtually impossible to maintain a strict accounting of the sharps used in a particular surgical procedure which is absolutely necessary to ensure that none remain in a patient after surgery.

It is also desirable that these surgical sharps be disposed in a manner which deters the casual scavenger intent on procuring hypodermic needles for illicit purposes.

Because many of these surgical sharps have tubular end sections which, after use, contain the bodily fluids of a patient, these used sharps pose additional risks to the surgical staff, especially if the sharps are disposed of in a manner which permits uncontrolled accumulation of such fluids during a surgical procedure. If the disposal container is accidentally bumped, jostled or otherwise knocked of a sterile table top, the accumulated fluids may splatter, causing operating room personnel to receive such fluids in an exposed area such as the eye. This is particularly dangerous to medical staff where the patient has a communicable disease.

It would thus be desirable to have a device for ensuring permanent disposition of used surgical sharps, including those with tubular end sections, in a safe and facile manner, while simultaneously ensuring that a strict accounting of the disposed sharps can be maintained.

SUMMARY OF THE INVENTION

It is therefore a primary object of the present invention to disclose and provide an apparatus for handling used surgical sharps, including those with tubular end sections, during and after a surgical operation in such a way that medical hazards are not presented to the operating room staff or to the patient.

It is a further object of the present invention to disclose and provide a means for ensuring the permanent disposal and non-reuse of hypodermic needles and the like.

It is also an object of the present invention is to provide and disclose such an apparatus in a low cost assembly.

These objects are preferably accomplished in a surgical instrument sharp end foil which can receive and permanently trap the free end of a surgical sharp.

Generally stated, the present invention is a surgical instrument sharp end foil comprising a housing, a gripping element for engaging the free end of the chosen sharp, a wedging element for engaging the gripping element, and a biasing element for urging the wedging element and the gripping element into engagement.

The wedging element is configured to communicate with the gripping element such that, upon insertion of the free end of the sharp into the housing, the gripping element exerts a force against the free end having a component which is perpendicular to the longitudinal axis of the sharp and such that a longitudinal movement of the sharp tending to withdraw the free end of the sharp from the housing causes the component of force perpendicular to the longitudinal axis of the sharp to increase so as to frictionally interfere with the withdrawal thereof.

More specifically, the housing of an exemplary embodiment has first and second substantially opposed ends and is provided with a sharps receiving portion at the first end. The sharps receiving portion includes a funnel-shaped sharps guide which terminates at an eccentrically located needle port. The needle port is sized to receive the free end of a syringe needle.

The housing of the exemplary embodiment is also provided with first and second substantially opposed lateral interior surfaces which extend between the needle port and the second end of the housing. The first lateral interior surface is tangent to the needle port and is provided for engagement with one side of the free end of the syringe needle. The second lateral interior surface includes a upper angled portion which inclines towards the first lateral interior surface as the upper angled portion extends towards the first end of the housing. The first lateral interior surface and the angled portion of the second lateral interior surface, together, comprise a wedging element which defines an area of convergence or a wedge zone.

Provided within the wedge zone is a movable gripping element. The movable gripping element is configured to ensure that the gripping element, in response to a biasing force, remains in simultaneous engagement with an opposing side of the free end of the syringe needle after insertion of the free end into the housing.

The exemplary foil is also provided with an elastomeric biasing element which constantly acts upon the movable gripping element, urging the gripping element towards the first end of the housing such that, after insertion of the free end of the syringe needle into the housing, the syringe needle is wedged between the gripping element and the first lateral interior surface.

With this configuration, any attempt to withdraw the syringe needle from the housing after insertion will generate opposing frictional forces at the interface between the first lateral interior surface and the free end and at the interface between the gripping element and the free end. The frictional force exerted by the free end upon the gripping element will tend to drive the gripping element upward towards the first end thereby increasing the opposing frictional forces acting upon the syringe needle thus further opposing withdrawal of the needle.

The foregoing needle retaining effect is enhanced by the provision, on the surface of the gripping element, of the plurality of evenly-spaced teeth which, upon application of a force tending to withdraw the syringe needle from the housing, are driven into the side of the syringe needle thereby creating a mechanical interference which precludes manual withdrawal of the needle.

The exemplary foil may also be provided with a sealing element, positioned within the housing between the biasing element and the second end, for engaging and sealing the tip of sharps having tubular end sections, wherein bodily fluids may reside.

A more complete understanding of the present invention will be afforded to those skilled in the art from a consideration of the following detailed description of the preferred exemplary embodiment thereof and to the appended sheets of drawings which will be described briefly hereafter.

BRIEF DESCRIPTION OF THE DRAWING

FIG. 1 is an exploded view of a preferred exemplary embodiment of the present invention, a surgical instrument sharp end foil, showing a housing, a gripping element, a biasing element and a sealing element.

FIG. 2 is a perspective view of the surgical sharp end foil of FIG. 1, positioned to receive the free end of a syringe needle through a funnel-shaped sharps guide;

FIG. 3 is a side section of the surgical sharp end foil of FIG. 1, showing the housing, the gripping element, the biasing element, and the sealing element in assembled relation.

FIG. 4 is a front section of the surgical sharp end taken through line 4—4 of FIG. 3.

FIG. 5 is the side section of the surgical sharp end foil of FIG. 3 after the free end of a syringe needle has been inserted therein; and FIG. 6 is a partial section of the surgical sharp end foil of FIG. 5 showing a preferred gripping element in engagement with an inserted syringe needle after attempted withdrawal of the syringe needle.

DETAILED DESCRIPTION OF EXEMPLARY PREFERRED EMBODIMENTS

Referring initially to the drawings, a preferred exemplary embodiment of the present invention is shown generally at 10. As best shown in FIGS. 2 and 5, the preferred exemplary embodiment is a surgical instruments sharp end foil configured to receive and permanently cap the free end of a typical syringe needle.

A typical syringe needle assembly 20 is shown generally at FIG. 2. Syringe needle assembly 20 includes a syringe needle 22 having a free end 24, a restrained end 25, an outer surface 26, and a longitudinal axis 27. Free end 24 is provided with a sharp tip 28 to facilitate invasive procedures. Syringe needle 22 typically is made of stainless steel and has an annular cross-section which defines a cylindrical cavity extending along longitudinal axis 27. It will be understood by those skilled in the art that syringe needle 22, as described, does not form a part of the present invention.

Referring now to FIG. 1, the preferred foil 10 includes a housing 30, a gripping element 70, a biasing element 80 and a sealing element 90. Housing 30 is provided in the form of a two-part plastic assembly composed of a first section 32 and a second section 34. Housing 30 includes first and second substantially opposed ends 36 and 38. A sharps receiving portion 100 is provided at first end 36.

As best shown in FIG. 3, housing 30 is also provided with a first set of substantially opposed lateral interior surfaces 40 and 42, an upper interior surface 44 and lower interior surface 46. As best shown in FIG. 4, housing 30 also includes a second set of substantially opposed lateral interior surfaces hereinafter referred to as interior sidewalls 48 and 50. Lateral interior surfaces 40 and 42 and interior sidewalls 48 and 50 each extend between upper and lower interior surfaces 44 and 46 to define interior cavity 60. Gripping element 70, biasing element 80 and sealing element 90 are provided therein.

Lateral interior surface 40 includes upper planar portion 52 and lower portion 54. As best shown in FIG. 5, upper planar portion 52 is configured to engage outer surface 26 of free end 24 along tangent 26A upon insertion of free end 24 into the foil 10. Lower portion 54 is configured to define a recess 62. Recess 62 is provided to facilitate the positioning of sealing element 90 adjacent lower interior surface 46 in a manner which ensures that, upon insertion of free end 24 into foil 10, tip 28 is fully ensconced with sealing element 90.

Lateral interior surface 42 includes an upper angled portion 56 and a lower planar portion 58. Upper angled portion 56 together with upper planar portion 52 comprise a wedging element 64 which is configured to communicate with gripping element 70 before and after insertion of free end 24 into foil 10. As best shown in FIG. 3, upper angled portion 56 inclines towards lateral interior surface 40 as upper angled portion 56 extends from lower planar portion 58 towards first end 36 to define an area of convergence or a wedge zone 66. Lower planar portion 58 is substantially parallel to upper planar portion 52.

Gripping element 70 is substantially cylindrical in shape, having two flat ends 72 and 74 and a substantially arcuate gripping surface 76 extending therebetween. As can be seen in FIG. 4, gripping element 70 is positioned within interior cavity 60 such flat ends 72 and 74 are adjacent interior sidewalls 48 and 50. The distance between sidewalls 72 and 74 is sufficient to permit gripping element 70 to slidably move within cavity 60 between upper and lower interior surfaces 44 and 46. Referring now to FIGS. 3 and 5, the dimensions of gripping surface 76 (vis-a-vis wedging element 64 and free end 24) are selected to ensure that gripping surface 76 (in response to the biasing action of biasing element 80) remains in simultaneous engagement with upper planar portion 52 and angled portion 56 before insertion of free end 24 into housing 30 and to ensure that gripping surface 76 (in response to the biasing action of biasing element 80) remains in simultaneous engagement with the outer surface 26 of free end 24 along tangent 26B and angled portion 56 after insertion of free end 24 into housing 30.

The provision of substantially arcuate gripping surface 76 facilitates the foregoing described purposes while at the same time ensuring that gripping element 70 does not engage free end 24 in such a manner as to prevent free end 24 from being fully inserted into the interior cavity 60 as best shown in FIG. 5. It will be understood by those skilled in the art that other configurations of gripping element 70 may also facilitate these purposes.

Critical to the operability of foil 10 is biasing element 80. In the preferred exemplary embodiment, biasing element 80 is composed of an annular shaped elastomer, having two ends 82 and 84, a substantially arcuate outer surface 86, and radial cavity 88 extending between ends 82 and 84. As best shown in FIG. 4, biasing element 80 is positioned within the interior cavity 60, between the gripping element 70 and sealing element 90, such that ends 82 and 84 are adjacent sidewalls 48 and 50 and outer surface 86 engages gripping element 70.

Referring now to FIGS. 3 and 5, the outer diameter (uncompressed) of biasing element 80 is sufficiently large to ensure that biasing element 80 constantly acts upon gripping element 70, urging gripping element 70 towards first end 36 such that the gripping surface 76 engages the upper planar portion 52 and angled portion 56 as described above.

Assembly of foil 10 is accomplished by compressing outer surface 86 of biasing element 80 sufficiently to enable gripping element 70, biasing element 80 and sealing element 90 to be inserted into interior cavity 60. Thereafter, first and second sections 32 and 34 of housing 30 are joined together using conventional means.

The interaction between the biasing element 80, the gripping element 70 and the wedging element 64 prior to insertion of free end 24 into interior cavity 60 is best shown in FIG. 3. Biasing element 80 exerts an upward force on gripping element 70 at the interface between gripping element 70 and biasing element 80. This upward force drives gripping element 70 into engagement with upper planar portion 52 and angled portion 56, effectively wedging gripping element 70 therebetween. The pressure exerted against gripping element 70 at the interface between gripping element 70 and angled portion 56 includes a component of force which is perpendicular to upper planar portion 52. This component of force is offset by an opposing force at the interface between gripping element 70 and upper planar portion 52.

As free end 24 is inserted into interior cavity 60, free end 24 is wedged between upper planar portion 52 and gripping element 70 thereby displacing gripping element 70 and causing gripping element 70 to move downwardly towards second end 38. As best shown in FIG. 5, free end 24 is engaged by upper planar portion 52 along tangent 26A and engaged by gripping element 70 along tangent 26B. The downward motion of gripping element 70 causes biasing element 80 to further compress thereby increasing the amount of pressure exerted by biasing element 80 against gripping element 70 at the interface between gripping element 70 and biasing element 80. This in turn increases the pressure at the interface between gripping element 70 and angled portion 56 which, in turn, increases the pressure at the interface between upper planar portion 52 and free end 24 along tangent 26A and at the interface between gripping element 70 and free end 24 along tangent 26B.

Any attempt to withdraw needle 22 from interior cavity 60 after insertion will generate opposing frictional forces at the interface between upper planar portion 52 and free end 24 and at the interface between gripping element 70 and free end 24. The frictional force exerted by free end 24 upon gripping element 70 will tend to drive gripping element 70 upward towards first end 36 thereby increasing the pressure exerted against the gripping element 70 at the inter-face between the gripping element 70 and the angled portion 56 which, in turn, will increase the pressure exerted both at the interface between upper planar portion 52 and free end 24 along tangent 26A and at the interface between gripping element 70 and free end 24 along tangent 26B, thereby increasing the needle retaining effect of foil 10. The greater the force applied to needle 22 tending to withdraw free end 24 from interior cavity 60, the greater the frictional forces exerted upon free end 24 resisting such movement.

Biasing element 80 is selected to ensure that a chosen surgical sharp may be manually inserted into interior cavity 60 without difficulty while at the same time ensuring that any attempt to withdraw such sharp will be opposed by sufficient frictional forces as described above. While, in the preferred exemplary embodiment, biasing element 80 must be sufficiently large to render foil 10 operable, biasing element 80 must not be so large as to prevent needle 22 from being inserted into interior cavity sufficiently to ensure that tip 28 fully engages sealing element 90. Preferably, then, outer diameter 87 (compressed) of biasing element 80 as measured in a plane transverse to upper planar portion 52 must be less than the distance between the tangent 26B to outer surface 26 and lower planar portion 54. To further facilitate complete engagement of tip 28 and sealing element 90, biasing element 80 may be positioned with interior cavity 60 vis-a-vis gripping element 70 such that the pressure at the interface between gripping element 70 and biasing element 80 urges biasing element 80 away from upper planar portion 52 as best shown in FIG. 5. Those skilled in the art will understand that alternative configurations, compositions and placements of biasing element 80 are possible and that alternative means may be employed to ensure that biasing element 80 does not unduly impede insertion of free end 24 into foil 10.

The needle retaining effect of the foregoing describe design is enhanced by the provision, on gripping surface 76, of a plurality of evenly-spaced teeth 78, each of which extends between ends 72 and 74. Teeth 78 are provided substantially sharp edges 79 and are backwardly curving, as best shown in FIG. 6, to improve the gripping characteristics of gripping surface 76. Teeth 78 (and the rest of gripping element 70) are preferably composed of a material which is hard enough to gouge the outer surface 26 of free end 24 such that, upon application of a force tending to withdraw needle 22 from interior cavity 60, teeth 78 are driven into outer surface 26 thereby creating a mechanical interference which precludes manual withdrawal of needle 24. The free end 24 of needle 22 is thus permanently engaged by foil 10. It will be understood by those skilled in the art that gripping surface 76 and upper planar portion 52 may, alternatively, be roughened or scored to improve the needle retaining effect of the present invention. , In order to ensure against the hazardous and uncontrolled accumulation of bodily fluids which may reside within used sharps having tubular end sections, e.g., hypodermic needles, foil 10 is also provided with sealing element 90. Upon insertion of free end 24 of needle 22 into interior cavity 60, tip 28 engages and becomes ensconced within sealing element 90 thereby retaining any such residual bodily fluids within the interior of the needle 22. Preferably, sealing element 90 is composed of a slab of material which is sufficiently soft to facilitate penetration of tip 28 into the sealing element 90 while at the same time ensuring a proper seal of the needle tip. In the exemplary embodiment, sealing element 90 is sized to complement lower interior surface 40 and to reside with recess 62. This placement of sealing element 90 ensures that, upon insertion of free end 24 into foil 10, tip 28 is fully ensconced with sealing element 90.

To facilitate operability of the preferred embodiment of the present invention, housing 30 is also provided with sharps receiving portion 100 at first end 36. As best shown in FIGS. 2, 3, and 4, sharps receiving portion 100 includes sharps guide 102. Sharps guide 102 defines a funnel-shaped recess having a maximum diameter 104 at first end 36 and a minimum diameter 106 between first and second ends 36 and 38. The minimum diameter 106 defines an eccentric needle port 108 which is sized to receive the free end 24 of syringe needle 22. Needle port 108 is positioned such that upper planar surface 52 is tangent to the outer diameter of needle port 108. This configuration enables the operator of syringe assemble 20 to place free end 24 through needle port 108 without difficulty while simultaneously ensuring that free end 24 will be properly positioned within the interior cavity 60 between upper planar portion 52 and gripping element 70.

It is contemplated that a plurality of foils 10 will be mounted in an array on a flat bottom foil container 20 which can be placed on a surgical table or other appropriate surface. The second end 38 of each foil 10 may be attached to the foil container, using any suitable means, so that the sharps receiving portion 100 of each foil 10 is directed substantially upward. Alternatively, the container may be provided with means to present the sharps receiving portions 100 at an angle to the horizontal to facilitate operability. The bottom of the container may be provided with an adhesive or other suitable means to ensure against unwanted movement during use.

It is seen therefore that a novel apparatus has been provided which readily enables surgeons and other operating room personnel to control used surgical sharps, including those with tubular end sections, during and after surgical operation in such a way that medical hazards are not presented to the operating room staff or to the patient while further ensuring the permanent disposal of hypodermic needles and the like.

Although the present invention has thus been described in detail with regard to the preferred embodiment and drawings thereof, it should be apparent to those skilled in the art that various adaptations and modifications of the present invention may be accomplished which still fall in the scope and spirit of the present invention. In particular, it will be appreciated by those skilled in the art that the surgical sharps contemplated for use with the present invention include conventional surgical implements which vary in size and shape depending upon the surgical application including without limitation trocars, stylers, blades and the like. Similarly, while the present invention contemplates the wedging of the free end of surgical sharp between gripping element 70 and a portion of wedging element 64, namely, upper planar portion 52, those skilled in the art will appreciate that alternative configurations of wedging means, biasing means and gripping means may be employed to generate compressive forces on the longitudinal surface of a surgical sharp which will increase in response to a longitudinal movement tending to withdraw the chosen sharp from the housing. Accordingly, the scope of the present invention is not limited to the specific embodiment as illustrated herein, but is limited only by the following claims and equivalents thereof.

What is claimed is:

1. In a surgical instruments system utilizing a surgical sharp such as a syringe needle wherein said surgical sharp has a free end and a restrained end opposite said free end and wherein said free end of said surgical sharp is contaminated upon use, the improvement comprising a foil for receiving and permanently capping said free end of said sharp after said use, said foil including mechanical gripping means for permanently engaging said free end of said sharp so as to prevent withdrawal of said free end of said sharp from said foil.

2. In a surgical instruments system utilizing a syringe needle to inject or withdraw fluids from a patient wherein said syringe needle has a free end and a restrained end opposite said free end, the improvement comprising a foil for receiving and permanently capping said free end of said syringe needle after use, said foil including mechanical gripping means for permanently engaging said free end of said sharp so as to prevent withdrawal of said free end of said sharp from said foil.

3. The surgical instruments system of claim 1 wherein said gripping means frictionally engages said free end of said sharp.

4. The surgical instruments system of claim 1 wherein said gripping means mechanically interferes with the withdrawal of said free end of said sharp.

5. The surgical instruments system of claim 1 wherein said free end of said sharp further comprises a tubular end section opposite said restrained end and said foil further comprises sharps tip enveloping means for sealing said tubular end section upon insertion of said free end of said sharp into said foil.

6. The surgical instruments system of claim 1 wherein said free end of said sharp further comprises a tubular end section opposite said restrained end and said foil further comprises a sealing element for sealing said tubular end section upon insertion of said free end of said sharp into said foil.

* * * * *